United States Patent
Hansen et al.

(10) Patent No.: US 11,200,710 B2
(45) Date of Patent: Dec. 14, 2021

(54) DEVICE AND METHOD FOR PET IMAGE RECONSTRUCTION

(71) Applicant: KØBENHAVNS UNIVERSITET, Copenhagen K (DK)

(72) Inventors: Thomas Mejer Hansen, Knebel (DK); Klaus Edvard Mosegaard, Copenhagen (DK); Knud Skou Cordua, Copenhagen (DK)

(73) Assignee: KØBENHAVNS UNIVERSITET, Copenhagen (DK)

( * ) Notice: Subject to any disclaimer, the term of this patent is extended or adjusted under 35 U.S.C. 154(b) by 86 days.

(21) Appl. No.: 16/615,352

(22) PCT Filed: May 18, 2018

(86) PCT No.: PCT/EP2018/063169
§ 371 (c)(1),
(2) Date: Nov. 20, 2019

(87) PCT Pub. No.: WO2018/215357
PCT Pub. Date: Nov. 29, 2018

(65) Prior Publication Data
US 2020/0202589 A1 Jun. 25, 2020

(30) Foreign Application Priority Data
May 24, 2017 (DK) .......................... PA 2017 70367

(51) Int. Cl.
G06T 11/00 (2006.01)
A61B 6/03 (2006.01)
A61B 6/00 (2006.01)

(52) U.S. Cl.
CPC ............ G06T 11/006 (2013.01); A61B 6/037 (2013.01); A61B 6/5258 (2013.01)

(58) Field of Classification Search
CPC .... G06T 11/0066; A61B 6/037; A61B 6/5258
See application file for complete search history.

(56) References Cited

U.S. PATENT DOCUMENTS

2011/0081068 A1* 4/2011 Brinks .................. G06T 11/005
382/132
2015/0145885 A1* 5/2015 Krol ......................... A61B 6/03
345/618

(Continued)

OTHER PUBLICATIONS

Robert M. Lewitt, Senior Member, IEEE, and Samuel Matej, Senior Member, IEEE (Overview of Methods for Image Reconstruction From Projections in Emission Computed Tomography) (Year: 2003).*

(Continued)

*Primary Examiner* — Khai M Nguyen
(74) *Attorney, Agent, or Firm* — Duane Morris LLP; Gregory M. Lefkowitz; Randall C. Pyles

(57) ABSTRACT

Disclosed is a device and a method for medical image reconstruction. The method comprises obtaining, image data of a medical scanner; obtaining a noise model for the image data from the medical scanner; obtaining an initial model indicative of expected image data properties; obtaining a mapping, wherein the mapping is indicative of a mapping from the medical scanner; determining a set of candidate images based on the image data, the noise model, the initial model, and the mapping; and determining and outputting a first representation of the image data based on the set of candidate images.

13 Claims, 3 Drawing Sheets

(56) References Cited

U.S. PATENT DOCUMENTS

2017/0294034 A1* 10/2017 Zhou .................... G06T 11/008
2017/0311918 A1* 11/2017 Qi ......................... A61B 6/032
2018/0293762 A1* 10/2018 Fu ........................... G06K 9/66
2021/0209817 A1* 7/2021 Pan ..................... A61B 6/5205

OTHER PUBLICATIONS

Robert M. Lewitt (Overview of Methods for Image Reconstruction From Projections in Emission Computed Tomography) (Year: 2003).*
Lewitt R M et al., "Overview of methods for image reconstruction from projections in emission computed tomography", Proceedings of the IEEE, IEEE. New York, US, (Oct. 2, 2003), vol. 91, No. 10, doi:10.1109/JPROC.2003.817882, ISSN 0018-9219, pp. 1588-1611, XP011100847 [X] 1-13 * abstract * * figures 1-6 * * Sections I-III and V* DOI: http://dx.doi.org/10.1109/JPROC.2003.817882.
Shepp L A et al., "Maximum Liklihood Reconstruction for Emission Tomography", IEEE Transactions on Medical Imaging, IEEE Service Center, Piscataway, NJ, US, (Oct. 2, 1982), vol. MI-01, No. 2, ISSN 0278-0062, pp. 113-122, XP000877028 [X] 1,13 * abstract * * figures 1-11 * * Sections I-IV *.
Wang Guobao et al., "PET Image Reconstruction Using Kernel Method", IEEE Transactions on Medical Imaging, IEEE Service Center, Piscataway, NJ, US, vol. 34, No. 1, doi:10.1109/TMI.2014.2343916, ISSN 0278-0062, (Jan. 2, 2015), pp. 61-71, (Dec. 24, 2014), XP011568804 [X] 1,13 * abstract *'figures 1-14 * * Sections I-IV* DOI: http://dx.doi.org/10.1109/TMI.2014.2343916.

* cited by examiner

DEVICE AND METHOD FOR PET IMAGE RECONSTRUCTION

CROSS-REFERENCE TO RELATED APPLICATIONS

This application is a § 371 national stage entry of International Application No. PCT/EP2018/063169, filed May 18, 2018, which claims priority to Denmark Application No. PA 2017 70367, filed on May 24, 2017, the entire contents of which are incorporated herein by reference.

The present disclosure relates to medical image reconstruction and in particular to device and method of positron emission tomography (PET) image reconstruction.

BACKGROUND

Medical imaging techniques are increasingly used within diagnostics, monitoring and research. Positron emission tomography (PET) is heavily exploited in clinical oncology in the search for, monitoring of, and imaging of tumors and metastases. Further, PET scanning is used as an important tool for clinical diagnosis of brain diseases and in general for mapping heart function and brain of humans.

Continuous efforts are made to increase the image quality of medical images and in particular PET images using image processing methods, however there is still a desire to improve the image quality of PET images.

SUMMARY

There is a need for devices and methods for improving image quality of medical scanning images.

Accordingly, a method for medical image reconstruction is provided, the method comprising obtaining image data from a medical scanner; obtaining a noise model for the image data from the medical scanner; obtaining an initial model indicative of expected image data properties; obtaining a mapping, wherein the mapping is indicative of a mapping of the medical scanner; determining a set of candidate images based on the image data, the noise model, the initial model, and the mapping or based on one or more of the image data, the noise model, the initial model, and the mapping; and determining and outputting a first representation of the image data based on the set of candidate images.

Further, a medical imaging device comprising a processor is provided. The processor is configured to obtain image data from a medical scanner; obtain a noise model for the image data from the medical scanner; obtain an initial model indicative of expected image data properties; obtain a mapping, wherein the mapping is indicative of a mapping of the medical scanner; and determine a set of candidate images based on the image data, the noise model, the initial model, and the mapping or based on one or more of the image data, the noise model, the initial model, and the mapping; and determine and output a first representation of the image data based on the set of candidate images. The processor may be configured to perform the method disclosed herein.

It is an important advantage that image data quality is improved, e.g. without introducing artefacts into the representation of the image data. Further, the present disclosure is in particular advantageous when monitoring the developments of a scanning subject, e.g. when monitoring size of a tumor in the scanning subject in order to evaluate whether the tumor is growing or shrinking.

It is an important advantage of the present disclosure that the image data are reconstructed based on a probabilistic approach enabling a more quantitative analysis of medical scanning images.

Further, the present disclosure presents an improved diagnostic tool for allowing medical staff to follow the developments of e.g. tumors in an improved way.

The disclosed system and method provide improved clinical decision-making.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
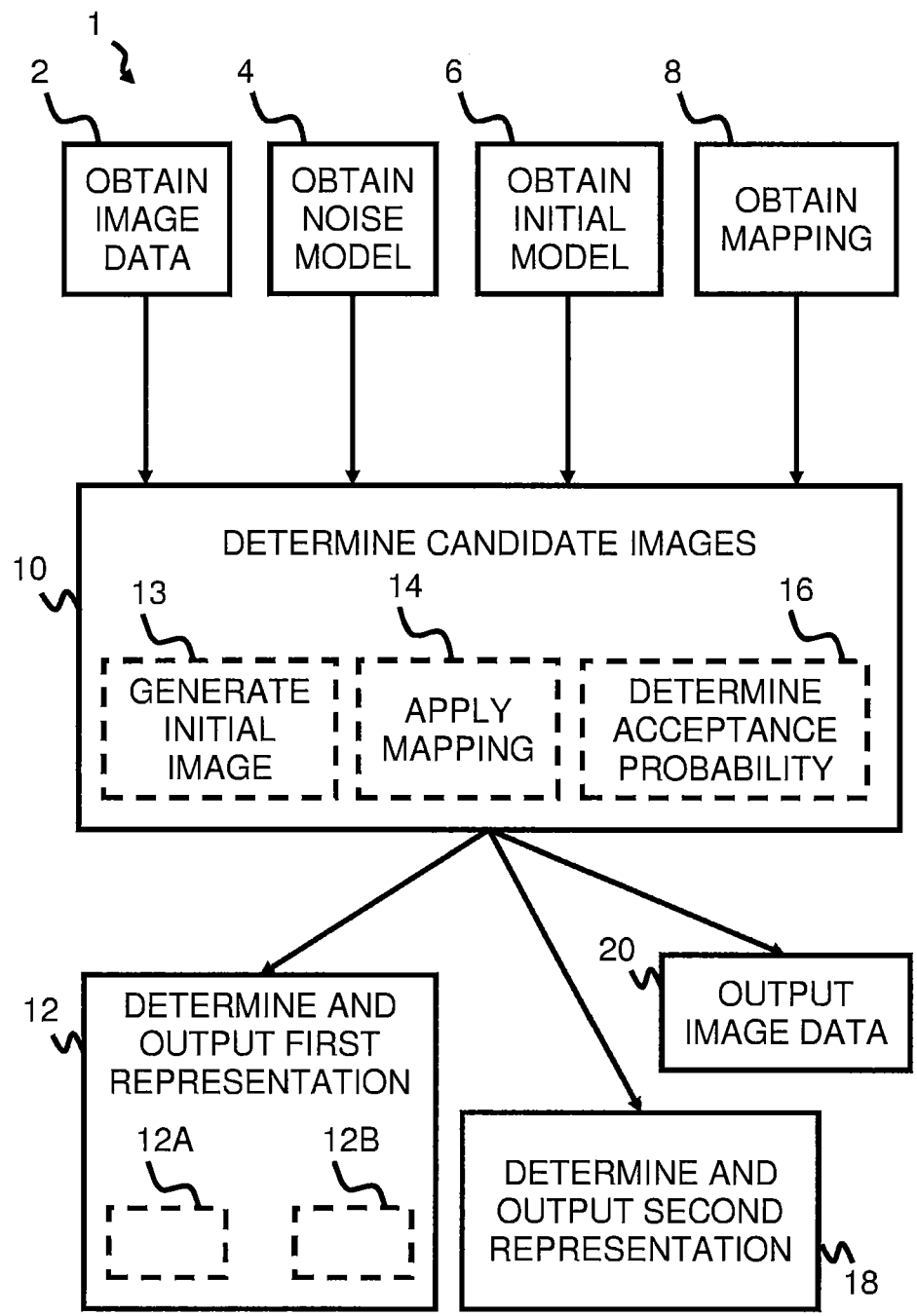
FIG. 1 is a flow diagram illustrating an exemplary method.

The present disclosure relates to a method for medical image reconstruction and medical imaging device. Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The method comprises obtaining image data from a medical scanner, such as a positron emission tomography (PET) scanner. The image data are also denoted I and may be image data of a scanning subject. The image data may comprise one or more scanning images from the medical scanner.

The method comprises obtaining a noise model for the image data from the medical scanner. The noise model is denoted N and may be a spatially correlated noise model, such as a 2D or 3D correlated noise model. The noise model describes or models the noise included in the image data. The noise model may be Gaussian model or other statistical model describing the noise of the image data. The noise model may be an uncorrelated noise model. The noise model may be obtained experimentally and/or analytically, e.g. based on an image recorded in an empty scanner and/or with a well-known subject.

The method comprises obtaining an initial model indicative of expected image data properties of the image data. For example, expected image data properties of the image data may comprise expected intensity levels (e.g. pixel levels), such as a plurality of predetermined intensity levels, such as two predetermined intensity levels, e.g. 0 or 1, or three predetermined intensity levels, e.g. 0, 0.5, 1, or four predetermined intensity levels. The initial model is denoted M and may be a spatially correlated model, such as a 2D or 3D correlated model. The initial model may be a 2D Gaussian model. The initial model may be a 3D multiple-point statistical model. The initial model may comprise an intensity distribution. The intensity distribution may define one or more events. The intensity distribution may comprise one or more intensity ranges. An event may be associated with or correspond to an intensity range. The initial model may comprise a reference image. The initial model may be a probabilistic model describing expected initial model properties from a medical expert. An initial model may be based on earlier image data of the scanning subject and/or medical observations from an expert. Obtaining an initial model may comprise obtaining a reference image from which an initial model, for example based on multiple point statistics, can be inferred. The reference image may be based on earlier image data of the scanning subject and/or an earlier first representation of image data.

In the method, obtaining an initial model indicative of expected image data properties may comprise obtaining a probability distribution. Obtaining an initial model may comprise obtaining a reference image from which an initial model, for example based on multiple point statistics, can be inferred.

The method comprises obtaining a mapping, also denoted L, wherein the mapping is indicative of a mapping of the medical scanner. The mapping of the medical scanner optionally maps an initial image (based on the initial model) to a noise free mapped initial image. The mapping may be obtained experimentally and/or analytically, e.g. based on an image recorded in an empty scanner and/or with a well-known subject. The observed image data I can then be described by the forward process $$I = L(T) + N,$$

where T is the scanning subject, L is the mapping of the medical scanner, and N is the noise.

The method comprises determining a set of candidate images, also denoted M_cand. Determining a set of candidate images may be based on one or more, e.g. all of, the image data, the noise model, the initial model, and the mapping. Determining a set of candidate images may comprise solving an inverse problem.

Determining a set of candidate images may comprise solving an inverse problem in a probabilistic setting, e.g. where a set of candidate images is generated from the probability distribution that combines all available information given as:

$$P_T(m) = k\, P_M(m) P_N(I - L(m))$$

Where $P_M(m)$ is a probability density representing the initial model M, $P_N(I-L(m))$ represents the noise model N, describing the residual $I-L(m)$, k is a constant, and m represents any initial image, e.g. an initial image sampled from an initial model M.

Determining a set of candidate images may comprise generating, e.g. sampling, an initial image and/or a plurality of initial images from the initial model. The set of candidate images may be based on the initial image and/or the plurality of initial images from the initial model. Determining a set of candidate images may comprise generating, e.g. sampling, an initial image and/or a plurality of initial images from the initial model and applying the mapping on the initial image and/or the plurality of initial images to obtain a mapped initial image and/or a plurality of mapped initial images. Determining a set of candidate images may comprise determining an acceptance probability and/or acceptance probabilities based on the mapped initial image and/or plurality of mapped initial images, the image data, and the noise model. Determining a set of candidate images may comprise determining an acceptance probability and/or acceptance probabilities indicative of a probability and/or probabilities of the difference between the image data and the mapped initial image and/or plurality of mapped initial images complying with the noise model. Determining the set of candidate images may be based on the acceptance probability and/or acceptance probabilities, e.g. the set of candidate images may be based on the acceptance probability and/or acceptance probabilities. An acceptance probability is indicative of how well a given mapped initial image matches the image data and a given noise model. Generating an initial image and/or a plurality of initial images may be based on a rejection sampling algorithm. An extended rejection sampling algorithm may be preferred. Generating an initial image and/or a plurality of initial images may be based on a Metropolis sampling algorithm and/or a Gibbs sampling algorithm. An extended Metropolis sampling algorithm may be preferred due to a reduction in the number of initial images needed for provision of a suitable result, e.g. by use of one or more suitable reference images. Generating an initial image and/or a plurality of initial images may be based on a Markov chain Monte Carlo sampling algorithm, see e.g. "Monte Carlo sampling of solutions to inverse problems", by Mosegaard and Tarantola, originally published in Journal of Geophysical Research, Vol. 100, No., B7, p 12,431-12,447, 1995.

The extended variations of the rejection sampling algorithm and the Metropolis sampling algorithm refer to methods in which the posterior probability, $P_T(m)$, need not be evaluated (as in the classical version of these algorithms). Instead, one must be able to sample from the $P_M(m)$ (the prior) and evaluate $P_N(I-L(m))$ (the data fit).

The extended rejection sampler comprises proposing an initial image m as an independent realizations of $P_M(m)$, also denoted the prior. The acceptance probability using an extended rejection sampler is given by $P\_acc = P\_N(I-L(m))$, and determines the probability with which m is accepted as an independent realization of $P_T(m)$.

The extended Metropolis algorithm is a Markov Chain in which an initial image m from the prior $P_M(m)$ is proposed based on a current initial image, m_current. The acceptance probability using extended Metropolis algorithm is given by $P\_acc = P\_N(I-L(m))/P\_N(I-L(m\_current))$, which determines whether the chain is allowed to move to the proposed initial image. If not, the chain stays at the current initial image. This approach will generate a series of dependent images that will represent a sample of $P_T(m)$. Correlation analysis can be performed in order find the number of independent realizations of $P_T(m)$ within this sample.

In the method, determining a set of candidate images may comprise generating an initial image and/or a plurality of initial images, e.g. based on the probability distribution and/or one or more reference images.

Determining the set of candidate images may comprise adding the initial image and/or the plurality of initial images to the set of candidate images with probability of the corresponding acceptance probability.

Determining a set of candidate images may comprise generating at least 100 initial images from the initial model.

Determining a set of candidate images may comprise generating at least 10,000 initial images from the initial model.

Accordingly, generating an initial image from the initial model and applying the mapping on the initial image to obtain a mapped initial image, determining an acceptance probability based on the mapped initial image, the image data, and the noise model, and adding the initial image to the set of candidate images with probability of the corresponding acceptance probability may be repeated at least 100 times, such as at least 10,000 times.

Generating an initial image from the initial model and applying the mapping on the initial image to obtain a mapped initial image, determining an acceptance probability based on the mapped initial image, the image data, and the noise model, and adding the initial image to the set of candidate images with probability of the corresponding acceptance probability may be repeated until a stop criterion is fulfilled, e.g. until the number of candidate images has reached a candidate image number threshold. The candidate image threshold may be 100, e.g. when a rejection sampling algorithm is used. The candidate image threshold may be 10,000, e.g. when a Metropolis sampling algorithm is used. The stop criterion may be based on a correlation analysis of the set of candidate images. The stop criterion may be selected such that any desired statistics based on the set of candidate images, such can be obtained with high confidence.

Obtaining an initial model indicative of expected image data properties may comprise quantifying a probability distribution. Determining a set of candidate images may comprise generating the initial images and/or the plurality of initial images may be based on the probability distribution.

The method comprises determining one or more representations, such as a first representation and/or a second representation.

Determining a first representation of the image data based on the set of candidate images may comprise calculating a first statistical measure based on the set of candidate images. Outputting a first representation of the image data based on the set of candidate images may comprise outputting the first statistical measure as the first representation. Determining a second representation of the image data based on the set of candidate images may comprise calculating a second statistical measure based on the set of candidate images. Outputting a second representation of the image data based on the set of candidate images may comprise outputting the second statistical measure as the second representation.

Determining a first representation may comprise calculating a mean of the candidate images, and outputting the mean of the candidate images as the first representation. The method may comprise outputting the image data.

Determining a representation may comprise determining a most likely pixel value for pixels of a representation image based on pixels of the candidate images, and wherein the representation comprises the representation image based on the most likely pixel values. For example, determining a first representation may comprise determining a most likely pixel value (e.g. 0 or 1, or any value therebetween), for pixels of a first representation image based on pixels of the candidate images, and wherein the first representation comprises the first representation image based on the most likely pixel values. The method may comprise determining and outputting a second representation of the image data based on the set of candidate images. The second representation may be different from the first representation. A pixel value may be associated or linked to an event. For example, a pixel value in a first pixel range (first pixel value) of low intensity may be linked to a first event, e.g. "No Tumor", and/or a pixel value in a second pixel range (second pixel value) of high intensity may be linked to a second event, e.g. "Tumor".

The method may comprise obtaining an event and optionally determining a probability or probability distribution of the event, e.g. based on the set of candidate images. The first and/or the second representation may be based on an event. An exemplary event may be "Tumor".

Determining a first and/or second representation may comprise obtaining a fractile, such as 0.5, 0.9 or 0.95, wherein the first and/or second representation is optionally based on the fractile. The fractile may be associated with an event. In an exemplary method, the second representation may be indicative of the 0.9 fractile of the event "Tumor", i.e. the second representation may indicate where 90% of the candidate images represents "Tumor".

FIG. 1 illustrates a flow diagram of an exemplary method for medical image reconstruction. The method 1 for medical image reconstruction comprises obtaining 2 image data I of a medical scanner; obtaining 4 a noise model N for the image data from the medical scanner; obtaining 6 an initial model indicative of expected image data properties, the initial model comprising a probability distribution; and obtaining 8 a mapping L, wherein the mapping L is indicative of a mapping of the medical scanner.

The method 1 comprises determining 10 a set M_cand of candidate images based on the image data I, the noise model N, the initial model M, and the mapping L; and determining and outputting 12 a first representation of the image data based on the set M_cand of candidate images.

The set of candidate images is determined by solving an inverse problem in a probabilistic setting, where a set of candidate images is generated as realizations from the probability distribution that combines all available information given as:

$$P_T(m) = k \, P_M(m) P_N(I-L(m))$$

Where $P_M(m)$ is a probability density representing the initial model M, $P_N(I-L(m))$ represents the noise model N, describing the residual I−L(m), and m represents any initial image, e.g. an initial image sampled from an initial model M. k is a constant.

Determining 10 a set of candidate images optionally comprises generating 13 an initial image m from the initial model M, applying 14 the mapping L on the initial image to obtain a mapped initial image; and determining 16 an acceptance probability p indicative of a probability of the difference between the image data I and the mapped initial image L(m) complying with the noise model N, and wherein determining the set of candidate images comprises adding the initial image m to the set M_cand of candidate images with probability of the corresponding acceptance probability p. In an exemplary method, determining a set of candidate images comprises generating at least 100, such as at least 1,000, or at least 10,000 initial images from the initial model.

In the method 1, determining 12 a first representation optionally comprises calculating 12A a mean of the candidate images in the set of candidate images, and outputting 12B the mean of the candidate images as the first representation.

Further, method 1 optionally comprises outputting 20 the image data and determining and outputting 18 a second representation of the image data I based on the set of candidate images.

Figure 2:
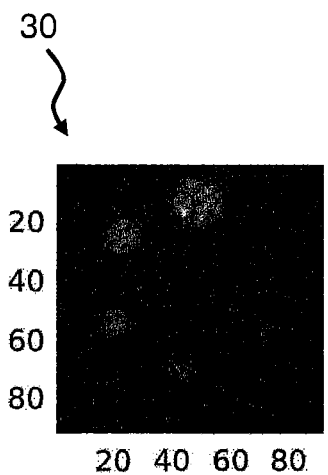
FIG. 2 shows exemplary image data, obtained from scanning six high intensity homogenous spheres in different sizes

FIG. 2 illustrates exemplary image data 30 being image data from a PET scanner. The image data is a 2D image with color-coded intensity, i.e. each pixel of the image data has an intensity value. The image data are generated based on a test model inserted in the scanning area of the PET scanner, the test model being made of six differently sized spheres arranged in a circular configuration.

Figure 3:
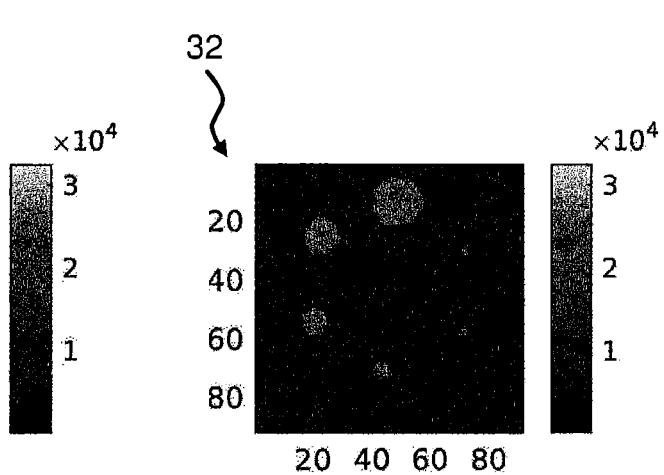
FIG. 3 shows an exemplary first representation based on the image data of FIG. 2.

FIG. 3 illustrates an exemplary first representation 32 of the image data 30 in FIG. 2, the first representation 32 being the output of method 1. The first representation is given as pixelwise mean of candidate images in the set of candidate images.

The set of candidate images is determined based on a 2D correlated Gaussian noise model, an initial model being a 2D correlated Gaussian probability distribution with a bimodal 1D marginal distribution. If $m_j^*$ represents one of NCI candidate images, the pixelwise mean (i refer to a specific pixel) is given by $$m_{mean}(i) = \frac{1}{NCI}\sum_{j=1}^{NCI} m_j^*(i)$$

Figure 4:
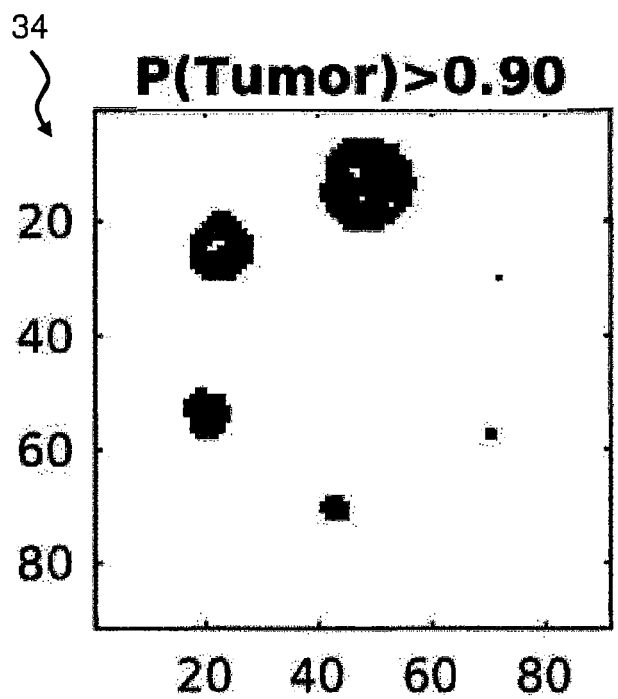
FIG. 4 shows an exemplary second representation based on the image data of FIG. 2.

FIG. 4 illustrates an exemplary second representation 34 of the image data 30 in FIG. 2, the second representation 34 being the output of method 1. The second representation indicates the pixels, where the number of pixel values (out of the NCI possible pixel values) represent high intensity or "Tumor" with a probability larger than 0.9 (0.9-fractile). This thus represents the locations/pixels with a tumor with 90% probability.

Figure 5:
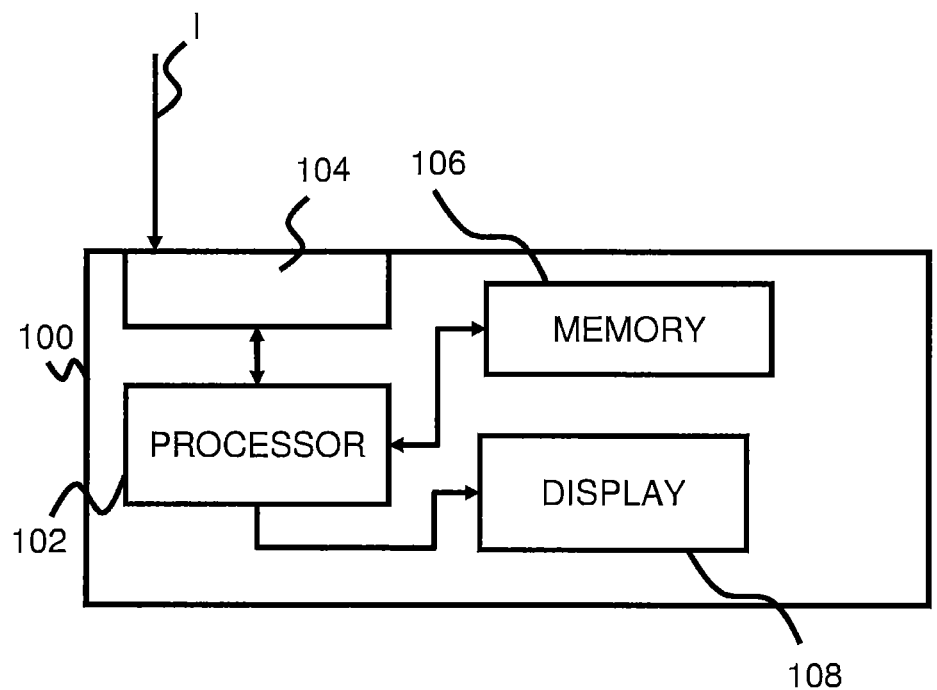
FIG. 5 schematically illustrates an exemplary medical imaging device.

FIG. 5 illustrates an exemplary medical imaging device. The medical imaging device 100 comprises a processor 102, an interface 104 connected to the processor 102, memory 106 connected to the processor 102, and optionally a display 108 connected to the processor 102. The processor 102 is configured to obtain, e.g. via interface 104, image data I of a medical scanner. The processor 102 is configured to obtain, e.g. via interface 104 and/or memory 106, a noise model for the image data from the medical scanner. For example, the processor 102 may receive a user selection of a noise model via the interface 104 and retrieve associated noise model parameters from the memory 106 based on the user selection. The processor 102 is configured to obtain, e.g. via interface 104 and/or memory 106, an initial model indicative of expected image data properties. The processor 102 is configured to obtain, e.g. via interface 104 and/or memory 106, a mapping, wherein the mapping is indicative of a mapping of the medical scanner; and determine a set of candidate images based on the image data, the noise model, the initial model, and the mapping. The processor 102 is configured to determine and output, e.g. via interface 104, to memory 106, and/or on display 108, a first representation and/or a second representation of the image data based on the set of candidate images.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

Exemplary methods and devices are disclosed in the following items:

Item 1. A method for medical image reconstruction, the method comprising
 obtaining image data of a medical scanner;
 obtaining a noise model for the image data from the medical scanner;
 obtaining an initial model indicative of expected image data properties;
 obtaining a mapping, wherein the mapping is indicative of a mapping from the medical scanner;
 determining a set of candidate images based on the image data, the noise model, the initial model, and the mapping; and
 determining and outputting a first representation of the image data based on the set of candidate images.

Item 2. Method according to item 1, wherein determining a set of candidate images comprises solving an inverse problem.

Item 3. Method according to any of items 1-2, wherein determining a set of candidate images comprises generating an initial image from the initial model, applying the mapping on the initial image to obtain a mapped initial image; determining an acceptance probability indicative of a probability of the difference between the image data and the mapped initial image complying with the noise model, and wherein determining the set of candidate images is based on the acceptance probability.

Item 4. Method according to item 3, wherein determining the set of candidate images comprises adding the initial image to the set of candidate images with probability of the corresponding acceptance probability.

Item 5. Method according to any of items 3-4, wherein determining a set of candidate images comprises generating at least 100 initial images from the initial model.

Item 6. Method according to item 5, wherein the determining a set of candidate images comprises generating at least 10,000 initial images from the initial model.

Item 7. Method according to any of items 1-6, wherein the noise model is a spatially correlated noise model.

Item 8. Method according to any of items 1-7, wherein determining a first representation comprises calculating a pixel wise mean of the candidate images, and outputting the mean of the candidate images as the first representation.

Item 9. Method according to any of items 1-7, wherein determining a first representation comprises determining a most likely pixel value for pixels of a first representation image based on pixels of the candidate images, and wherein the first representation comprises the first representation image based on the most likely pixel values.

Item 10. Method according to any of items 1-9, wherein the method comprises obtaining an event and determining a probability of the event based on the set of candidate images.

Item 11. Method according to any of items 1-9, wherein obtaining an initial model indicative of expected image data properties comprises quantifying a probability distribution, and wherein determining a set of candidate images may comprise generating initial images based on the probability distribution.

Item 12. Method according to any of items 1-11, wherein the method comprises determining and outputting a second representation of the image data based on the set of candidate images.

Item 13. Medical imaging device comprising a processor, wherein the processor is configured to:
  obtain image data of a medical scanner;
  obtain a noise model for the image data from the medical scanner;
  obtain an initial model indicative of expected image data properties;
  obtain a mapping, wherein the mapping is indicative of a mapping from the medical scanner; and
  determine a set of candidate images based on the image data, the noise model, the initial model, and the mapping; and
  determine and output a first representation of the image data based on the set of candidate images.

LIST OF REFERENCES

1 method for medical image reconstruction
2 obtaining image data
4 obtaining a noise model
6 obtaining a set of initial models
8 obtaining a mapping
10 determining a set of candidate models
12 determining and outputting a first representation
14 applying the mapping
16 determining probability parameters
18 determining and outputting a second representation
20 outputting image data
30 image data
32 first representation of image data
34 second representation of image data
100 medical imaging device
102 processor
104 interface
106 memory
108 display
I image data
L mapping
M initial model
$m_1$ I'th initial image
M_cand set of candidate images
$m_j$ j'th candidate image
N noise model
$p_i$ i'th acceptance probability of the i'th mapped initial image

The invention claimed is:

1. A method for medical image reconstruction, the method comprising
  obtaining image data from a medical scanner;
  obtaining a noise model for the image data from the medical scanner;
  obtaining an initial model indicative of expected image data properties;
  obtaining a mapping, wherein the mapping is indicative of a mapping of the medical scanner;
  determining a set of candidate images comprising generating a plurality of initial images from the initial model, and wherein the set of candidate images are based on the image data, the noise model, the plurality of initial images from the initial model, and the mapping; and
  determining and outputting a first representation of the image data based on the set of candidate images.

2. Method according to claim 1, wherein determining a set of candidate images comprises solving an inverse problem.

3. Method according to claim 1, wherein determining a set of candidate images comprises applying the mapping on the plurality of initial image to obtain a plurality of mapped initial images; determining acceptance probabilities indicative of a probabilities of the difference between the image data and the plurality of mapped initial images complying with the noise model, and wherein the set of candidate images is based on the acceptance probabilities.

4. Method according to claim 3, wherein determining the set of candidate images comprises adding the initial image to the set of candidate images with probability of the corresponding acceptance probability.

5. Method according to claim 3, wherein determining a set of candidate images comprises generating at least 100 initial images from the initial model.

6. Method according to claim 5, wherein the determining a set of candidate images comprises generating at least 10,000 initial images from the initial model.

7. Method according to claim 1, wherein the noise model is a spatially correlated noise model.

8. Method according to claim 1, wherein determining a first representation comprises calculating a pixel wise mean of the candidate images, and outputting the mean of the candidate images as the first representation.

9. Method according to claim 1, wherein determining a first representation comprises determining a most likely pixel value for pixels of a first representation image based on pixels of the candidate images, and wherein the first representation comprises the first representation image based on the most likely pixel values.

10. Method according to claim 1, wherein the method comprises obtaining an event and determining a probability of the event based on the set of candidate images.

11. Method according to claim 1, wherein obtaining an initial model indicative of expected image data properties comprises quantifying a probability distribution, and wherein determining a set of candidate images may comprise generating the plurality of initial images based on the probability distribution.

12. Method according to claim 1, wherein the method comprises determining and outputting a second representation of the image data based on the set of candidate images.

13. Medical imaging device comprising a processor, wherein the processor is configured to:
  obtain image data from a medical scanner;
  obtain a noise model for the image data from the medical scanner;
  obtain an initial model indicative of expected image data properties;
  obtain a mapping, wherein the mapping is indicative of a mapping of the medical scanner; and
  determine a set of candidate images comprising generating a plurality of initial images from the initial model, and wherein the set of candidate images are based on the image data, the noise model, the plurality of initial images from the initial model, and the mapping; and
  determine and output a first representation of the image data based on the set of candidate images.

* * * * *